US012151093B2

United States Patent
Horn

(10) Patent No.: US 12,151,093 B2
(45) Date of Patent: Nov. 26, 2024

(54) PUMP FOR SUPPORT OF THE HEART

(71) Applicant: Franz-Harro Horn, Tating (DE)

(72) Inventor: Franz-Harro Horn, Tating (DE)

(73) Assignee: RAP-P Meditec UG (haftungsbeschränkt), Tating (DE)

( * ) Notice: Subject to any disclaimer, the term of this patent is extended or adjusted under 35 U.S.C. 154(b) by 420 days.

(21) Appl. No.: 17/541,302

(22) Filed: Dec. 3, 2021

(65) Prior Publication Data

US 2022/0176099 A1 Jun. 9, 2022

(30) Foreign Application Priority Data

Dec. 3, 2020 (DE) .......................... 102020132226.7

(51) Int. Cl.

| | |
|---|---|
| *A61M 60/812* | (2021.01) |
| *A61M 60/221* | (2021.01) |
| *A61M 60/422* | (2021.01) |
| *A61M 60/538* | (2021.01) |
| *A61M 60/816* | (2021.01) |
| *A61M 60/89* | (2021.01) |

(52) U.S. Cl.
CPC ........ *A61M 60/812* (2021.01); *A61M 60/221* (2021.01); *A61M 60/422* (2021.01); *A61M 60/538* (2021.01); *A61M 60/816* (2021.01); *A61M 60/89* (2021.01); *A61M 2205/103* (2013.01); *A61M 2205/3317* (2013.01)

(58) Field of Classification Search
CPC ... F04C 13/001; F04C 15/064; A61M 60/258; A61M 60/422
See application file for complete search history.

(56) References Cited

U.S. PATENT DOCUMENTS

| | | | | |
|---|---|---|---|---|
| 2,501,947 | A * | 3/1950 | Johnson ................ | F04C 2/3566 418/240 |
| 2017/0189593 | A1* | 7/2017 | Wappenschmidt .......................... | A61M 60/258 |

FOREIGN PATENT DOCUMENTS

| | | |
|---|---|---|
| DE | 6927594 U | 8/1971 |
| DE | 102004005468 B4 | 8/2005 |
| DE | 202016000016 U1 | 3/2016 |

* cited by examiner

*Primary Examiner* — Michael J D'Abreu
(74) *Attorney, Agent, or Firm* — Michael Soderman

(57) ABSTRACT

Rotary lobe pump, comprising a pump housing (2, 9, 10) with a substantially cylindrical pump chamber (8) and a rotary lobe as rotor (1) with at least two blades (3) arranged opposite each other or evenly distributed in the circumferential direction and at least one sealing valve (4), characterized in that at least two sealing valves (4a, 4b) arranged opposite one another or uniformly distributed in the circumferential direction are provided, the at least two sealing valves (4a, 4b) being rotatable or pivotable, and an inlet duct (11) to at least two inlet openings (6) into the pump chamber (8) and an outlet duct (12) from at least two outlet openings (7) out of the pump chamber (8) being provided axially in a rotor axial tube (18), extending from the opposite axial ends and separated from one another.

17 Claims, 6 Drawing Sheets

Section through Fig. 3

PUMP FOR SUPPORT OF THE HEART

CROSS REFERENCE TO RELATED APPLICATIONS

This application claims the priority of DE 102020132226.7 filed on 2020 Dec. 3; this application is incorporated by reference herein in its entirety.

BACKGROUND

The invention relates to a mechanical circulatory support device. The pump is intended to reproduce a pulse beat and to support the blood flow in a very gentle manner.

Intensive work is being done around the world on a device for mechanical support for patients with cardiac insufficiency, even including a partial technical heart replacement.

Systems for adjusting the pulse rate have solutions, for example, with rubber-like pumping chambers or membranous foils which are subject to material aging and therefore to wear and tear. That is why, for example, simple centrifugal pump systems are used today which, however, largely thanks to their simplicity, only generate a pulse-free and thus steady even blood flow which, if necessary or only to some extent, can generate various waves of pressure as needed based on variable rotational speed increases to come closer to the effect of the pulse. Here, one must consider that high rotational speeds have a quite negative effect on capacity and thus arterial blood transport. However, such technical constructions work solely with metallic or ceramic materials which are not subject to wear and tear, which has led to their current use in such solutions as those in centrifugal systems.

In centrifugal pump systems, however, due to a high rotational speed, the result is radial turbulence in the suction area around the suction vector with subsequent further strong radial acceleration due to the rapidly rotating drive rotor in the actual pump body.

Rotary lobe pumps with two intermeshed rotary lobes or one rotary lobe and a sealing valve are known from hydraulic pump construction. Also known are blade pumps which have an alternating rotary pivoting movement of a blade with valve flaps in the blade and in the pump housing for inlet and outlet. The problem with known pumps is that flow-free dead spaces can form, so that when they are used as blood pumps, there is a risk of blood clots and/or plaque formation.

Known, for example, from DE 10 2004 005 468 B4 is a rotary lobe machine, usable as a pump for liquids, which has a working rotor and a sealing rotor, whereby the fluids to be conveyed are fed in via a hollow, central shaft. A disadvantage of this is the associated large size.

Additionally, from DE6927594U a rotary lobe pump with a rotary lobe and a sealing valve is known.

Also known from DE202016000016U1 is a rotary lobe pump with a rotary lobe and at least two external rotors in a pump housing.

SUMMARY

The objective of the invention is to create a rotary lobe pump or rotary blade pump which is membrane-free and capable of readjusting a pulse during pumping operation.

The instant application involves a rotary lobe pump, comprising a pump housing (2, 9, 10) with a substantially cylindrical pump chamber (8) and a rotary lobe as rotor (1) with at least two blades (3) arranged opposite each other or evenly distributed in the circumferential direction and at least one sealing valve (4), characterized in that at least two sealing valves (4a, 4b) arranged opposite one another or uniformly distributed in the circumferential direction are provided, the at least two sealing valves (4a, 4b) being rotatable or pivotable, and an inlet duct (11) to at least two inlet openings (6) into the pump chamber (8) and an outlet duct (12) from at least two outlet openings (7) out of the pump chamber (8) being provided axially in a rotor axial tube (18), extending from the opposite axial ends and separated from one another, one of the inlet openings (6) being arranged behind each one of the blades (3) in the direction of rotation (14) and one of the outlet openings (7) being arranged in front of each blade in the direction of rotation (14) in the rotor axial tube (18).

DETAILED DESCRIPTION

The object of the invention is to create a rotary lobe pump or rotary blade pump which is membrane-free and capable of achieving gentle conveyance of the relevant fluid, for example blood, while establishing a pulse during pump operation.

It has been shown that rotary lobe pumps or rotary blade pumps with a special rotary lobe with at least two blades and at least two sealing valves are well suited as cardiac pumps.

The rotary lobe pump or rotary blade pump according to the invention can reproduce a pulse during its pumping work. The special basic conditions of a device that replaces a human heart can be taken into account.

In the current application, the invention achieves that a rotary lobe pump or rotary blade pump comprising a pump housing with an essentially cylindrical pump chamber and a rotary lobe as a rotor with at least two blades arranged opposite one another or evenly distributed in the circumferential direction, a rotor axle tube and at least one sealing valve is created, with at least two sealing valves arranged opposite one another or evenly distributed in the circumferential direction, and with the at least two sealing valves being rotatable or pivotable, and with an axially positioned inlet duct to at least two inlet openings into the pump chamber and an axially positioned outlet duct from at least two outlet openings from the pump chamber in the rotor axle tube, said ducts extending from the opposite axial ends in the rotor axle tube and separated from each other, one of the inlet openings being arranged behind each one of the blades in the rotor axle tube in the direction of rotation and one of the outlet openings being arranged in front of each blade in the direction of rotation. Here, rotatable or pivotable also includes moveable or turnable.

Regarding the direction of rotation, a pressure side or outlet side or a corresponding area is formed in front of the respective blade and, in the direction of rotation, a suction side or inlet side or a corresponding area is formed behind the respective blade.

Additionally, the invention comprises a method for operating a rotary lobe pump or rotary blade pump, in particular as a cardiac pump to support the human heart or as a heart substitute, in which in an essentially cylindrical pump chamber of a pump housing, through the rotary movement of a rotary lobe as a rotor with a rotor axle tube and with it at least two blades arranged opposite each other or evenly distributed in the circumferential direction, a fluid is pressed into an outlet opening in the rotor axle tube in the direction of rotation in front of the respective blade and at the same time the fluid is sucked in through an inlet opening in the rotor axle tube in the direction of rotation behind the respective blade, with a separation of the areas of the pressure and suction being effected in each case by means of a sealing valve and the respective sealing valve being in a closed position for the pressure or outlet and the suction or inlet, and after the pressure or outlet and the suction or inlet the respective sealing valve is pivoted to the radially outer area of the pump chamber or rotated around the radially outer end of the respective blade to allow the respective blade to pass, and when the blade has passed, the respective sealing valve is brought or moved back into a closed position on the rotor axle tube, so that the pump chamber closes again in the areas delimited in the circumferential direction for pressure or outlet and suction or inlet, whereby the blood conveyance or the pressure or outlet and the suction or inlet is performed again in a clocked fashion. By the respective blade passing the respective sealing valve, which must evade, the blood flow is completely interrupted until the blade has passed or proceeded through the area of the sealing valve, and the sealing valve then closes again or moves toward closure.

According to the invention, a rotor with at least two blades is arranged in the substantially cylindrical pump chamber of the pump housing, for example with a front and rear housing cover, which rotor moves blood by means of its rotation.

Advantageously, in the pump presented here, the fluid is moved largely only in a laminar manner, in some cases deliberately accelerated and also pressed in the pump during pumping similarly to the way this occurs in a natural heart and ejected in an accelerated manner.

An extreme rotating turbulence that traumatizes the blood as in the known centrifugal pumps, VAD pumps, with an average of 5000 rpm of the rotor, does not occur. However, a swirling flow of blood very close to that of a healthy heart into the vascular system is certainly achieved. This phenomenon can be observed in all natural processes with regard to fluids, meandering rivers, or streams of gases. In the healthy body, this process of slight swirling takes place, whereby the blood is prevented from forming clots or plaque by swirling gently in all directions.

The pump rotates at 35 rpm, a half revolution conveying $2\times35$ cm$^3$=70 cm$^3$/pulse beat. The rotor conveys the blood by a rotating movement over a rotational angle range of approx. 140° per pulse beat within a half revolution or within an angle of rotation of 180° in only 0.24 seconds. A half revolution corresponds to a pulse rate corresponding to an average of 70 beats per minute. In general, through its moderate rotation, this type of pump transfers such rotation to the medium to be conveyed, which is of great importance for the anatomy of blood movement and thus contributes to the prevention of clot and plaque formation. Advantageously or preferably, the outlet duct or the rotor axle tube for the outlet or the outlet tube additionally has a winding or helical course or internal cross section.

The fluid traverses its flow through clearly specified guide cross-sections without sharp edges etc. At, for example, 35 rpm or 70 pulse beats per minute, the blood cannot suffer any significant damage. Only when the blade passes relatively slowly under the sealing valve does the blood swirl on all sides, but this is very deliberate but moderate, thus preventing thickening or plaque formation. The movements of the components are, however, comparatively calm movements of very smooth surfaces in the blood medium, which at this point are deliberately designed to wash freely around the valve as well as the blade in all directions.

The rotary lobe pump or rotary blade pump according to the invention has at least two sealing valves. Based on the interruption of the conveying capacity by said sealing valve that opens to let the blade pass, but otherwise representing the temporal and/or spatial limitation of the pump chamber with the pump chamber sections, the result is a clocking or pulsing of the fluid as conveyed material.

For this medical purpose, it functions as a pulsating blood conveying pump, i.e., a partial or unilateral cardiac support or even a complete heart replacement, doing the work for both chambers of the heart. The vascular system is subjected to distension and complete relief by the pulse emitted by the pump, similar to the work of the natural heart. In this way, not only the vascular system but also the ventricular system is kept elastic and pulsating.

It is advantageous for the outlet duct and inlet duct, which are separate from one another, each extending from the opposite axial ends of the rotor axle tube, and for the inflow and outflow of the fluid that the rotor axle tube is divided axially into two sections, with a flow-optimized duct separation being present that is transverse to the axial extension of the rotor axle tube, for example inclined, also rounded as well as curved, with the inlet duct thus forming an inflow duct from one axial end into the rotor axle tube and the outlet duct forming an outflow duct from the opposite axial end of the rotor axle tube, with the fluid flowing through the inlet duct as an inflow duct via the inlet openings and reaching the pump chamber and the fluid leaving the pump chamber again through the outlet openings into the outlet duct as an outflow duct. This means that the connections for the inflow and outflow of the fluid are in one line.

The rotary lobe pump or rotary blade pump according to the invention provides support for the human heart or allows a heart to be partially replaced by an artificial replacement. The rotary lobe pump according to the invention provides a basic pulse rate similar to that of a healthy heart, e.g., close to 70 pulse beats/min, by pumping via a drive an electronically controlled delivery volume of, for example, approx. 70 cm$^3$ per revolution, which is determined or designed depending on the patient, and thus about 4,900 cm$^3$/min of blood. Depending on the performance requirements, the fresh blood supply can be adapted to the respective body and pulsed variably into the bloodstream.

The simple construction actually comprises three moving rotating or partially rotating parts, including the rotor with blades and the two sealing valves, and a substantially circular, cylindrical pump housing made of metallic or other non-aging materials.

The rotary lobe pump or rotary blade pump according to the invention makes it possible to provide a basic pulse rate similar to that of a healthy heart in normal pulse mode with approx. 70 pulse beats per minute, but also with a significantly increased or reduced delivery rate, set by the rotational speed.

The active discharge of the blood from the rotary lobe pump or rotary blade pump follows, for example, directly the specification from the sinus node, which is digitally transferred to the control unit and passed on as an electrical command.

The delivery volume can be adjusted for both small and large hearts as well as for larger or smaller delivery volumes by adapting the size of the pump chamber in terms of length or its diameter to the desired delivery volume of the specific patient, so that easily scalable, varying performance sizes are available for use.

The rotational speed of the pump can also be adjusted based on the oxygen demand to be measured or other physiological parameters so that the pulse, similar to that of a human heart, can adapt briefly or permanently to increased physical exertion or performance requirements, if such physiological information is provided in terms of measurement technology and, for example, by means of software, a higher rotational speed is specified for the drive, for example the rotating field of an electric motor, in software and hardware.

To simplify the structural design, a simple rotor bearing is provided if the rotor, for example, provides two blades at 0° and at 180° with respect to one revolution or the full circle and thus the desired delivery volume can be pumped or moved per half revolution and the arrangement divides of the rotor blades divides the pump chamber into, for example, two delivery halves, so that two separate delivery areas each provide the predetermined volume over half a revolution and the rotor axle tube has a duct separation in the middle in axial extension. In this solution with two opposite conveying sections, unlike the one-sided pressure that occurs in a rotor with only one blade, the pressure that occurs is canceled out, whereby the rotor is guided floating with its two blades and thus only a simple bearing solution needs to be provided.

The rotor axle tube of the rotor can be mounted in the pump housing, for example, on two housing halves or on two housing covers on one housing or on a concentrically arranged centering or guide axis or shaft or in another suitable manner.

The rotor axle tube can run on the surface of the respective housing component or be supported in a recess or protrude into corresponding openings of the inlet or outlet and be supported there.

In the pump housing, the blades form a first and second delivery area, each over an area of half a revolution of the rotor. The volume is, for example, twice approx. 35 cm³ per half revolution, so that 70 cm³ can be pumped per beat.

Additionally, magnets are optionally provided on the blades and on the pump housing on the housing wall and/or the housing covers, for example circumferential electromagnets on the two housing surfaces present in the axial direction. Through the arrangement of magnets or the electromagnets and their activation, the rotor can also be centered purely on electromagnetic-electronic measurement, in that a corresponding activation is effected through an associated increased or decreased power application to the electromagnets. Furthermore, varying rotational speeds of the rotor can also be achieved as a function of increasing or decreasing blood quantity requirements.

If a rotor with only one blade is used, it would have to be placed on bearings, because the pressure work exerts a not inconsiderable lateral pressure on the rotor and, without a bearing, the function of an undisturbed rotor rotation would not be guaranteed.

Furthermore, the pump housing can be constructed in several parts. For example, the pump housing can be formed or assembled in several parts by two housing halves or with two housing covers on one housing or in some other way.

A sealing rotor can advantageously be dispensed with, significantly reducing the size of the artificial heart. Instead of the sealing rotor, the sealing valves are used, which are preferably curved or sickle-shaped or omega-shaped and form the delimitation of the pump chamber and the respective pump chamber section. This achieves a smaller size. The sealing valves can be controlled and moved synchronously, e.g., via a mechanical or electro-mechanical or magnetic drive in or on the pump housing, for example in or on the housing cover(s), to allow the blade to pass and then close again. The movement of the sealing valve depends on the angular speed of the rotor or on the angle of rotation of the blades and thus the rotor.

Preferably, two of the rotary lobe pumps can be cascaded or arranged in combination, so that, for example, different fluids or the same fluid can be pumped in parallel with several rotary lobe pumps. A combination as a double pump is possible. As cardiac replacement or cardiac support, fresh blood is taken over from the pulmonary vessels and axially passed into the aorta. The parallel pump takes over old blood from the venae cavae and conducts it into the pulmonary arteries. These functions can also be implemented with only one common rotor axle or rotor shaft. Thus, two pumps can work synchronously, either on common a rotor axle or rotor shaft or each on its own rotor axle or rotor shaft and separate or offset from each other.

A further aspect of the invention allows that two pumps are coupled, provided with one common rotor axle or rotor shaft. One of the two pumps with its rotor axle tube takes over the blood from the pulmonary veins and guides it through the pump chamber into the other end of the rotor axle tube and from there into the aorta. Likewise, the blood of the venae cavae is fed into the rotor axle tube of the other pump. After passing through the second or other pump chamber, it is also fed back into the other end of the rotor axle tube and passed into the pulmonary arteries. This means that two pumps on one rotor axle tube or rotor axle shaft can work together and synchronously but separately. The exit of the blood from the outlet tube into the respective blood vessel is designed in such a way that it clearly harmonizes congruently with the pulse.

The terms rotational speed or angular speed of the rotor or its blades are understood to be synonymous.

Due to the shape of the rotor and the blades, the rotary lobe pump can also be referred to as a rotary blade pump or represents a rotary blade pump. Thus, the two names can be used synonymously.

Any liquids, including blood or other bodily fluids that can be pumped, are understood to be a fluid.

Advantageous embodiments of the rotary lobe pump and the method are presented in the subclaims.

Since the blades are point-symmetrical with respect to the axis of rotation of the rotor axle tube, blades that are flow-optimized and that are adapted to the liquid can advantageously be provided.

The displacement of the fluid can be optimized by the contour of the blades having a single or multiply curved course in a radial direction. Particularly in the area in front of and on the sealing valves, the displacement of the amount of fluid can be optimized by appropriate shaping to make the overall size of the pump as small as possible. Due to anatomical peculiarities or because of space limitations, for example, in a human chest cavity, a small size is preferred.

Advantageously, the contour of the at least two sealing valves in a radial direction of the pump housing has a curved or circular arc shape. In terms of the force exerted by pressure or outlet and suction or inlet during pumping, the distribution of forces is thus optimized. Furthermore, the displacement of the fluid can be further optimized, in particular in cooperation with the respective blade of the rotor. The respective sealing valves are thus flat or partial cylinder jacket shaped over the area or circumferential section of the circular arc.

By the curved course of the contour of the blades in a radial direction and the curved course of the contour of the at least two sealing valves being similar or adapted or congruent to each other, the displacement of the fluid in interaction with the respective blade of the rotor can be further optimized.

By the at least two sealing valves having at the end facing the radially outer housing wall of the pump chamber an approximately tangentially straight extension or an extension with a or the radius of the inlet or outlet corresponding to the pump chamber outer diameter of the housing wall of the pump chamber or one or the pump chamber outer diameter, the respective blade can still perform pumping work while it is already in the area of the sealing valve or omega valve without the latter already being open or having to open. This minimizes the time span or the angle of rotation in which the pump does not or cannot do any pumping work. Another advantage is that the total volume of the pump can be reduced while the pump output remains the same. Furthermore, the passage or entry of the respective blade into the area of the respective sealing valve is promoted. Additionally, the sealing effect on the radially outer wall of the pump housing and on the rotor axle tube is improved.

By the at least two sealing valves being slidably or rotatably or pivotably mounted or arranged in or on the pump housing via spokes or webs or pins or balls at a pivot point or swivel point or in rails or in or on guides, the pump housing having at least some free space radially and/or axially at least in some areas in the region or range of movement of the at least two sealing valves, i.e. the pump housing being widened in this region, the sealing valves can be optimally mounted and moved or deflected for the passage of the respective blade. Also, the free space that is created when the respective sealing valve opens forces and promotes swirling of the fluid laterally, above and below the sealing valve in the area of the bearing and guidance and thus in the area of the widening of the pump housing.

By the at least two sealing valves being concentrically or eccentrically rotatable or pivotable or turnable, with the at least two sealing valves in a closed position abutting radially and axially against the pump housing and in an open position being spaced from the pump housing, the position or the distance of the sealing valves to the pump housing can be increased, whereby a flow around and turbulence of the fluid in the boundary region between sealing valve and pump housing is favored. Particularly when handling or pumping blood, precautions must be taken to avoid dangerous blood clots. To this end, it is important that there is no area where the blood flows slowly or does not flow at all.

Preferably, the at least two sealing valves have a sickle-shaped or omega-shaped course in the radial direction. The sealing valve can therefore also be referred to as an omega valve. It thus has an optimized course in cooperation with the blades of the rotor.

The terms sealing valve and omega valve are also used synonymously for the sake of simplicity, so that an omega valve is understood to mean a sealing valve and a sealing valve also means an omega valve.

Preferably, the construction of the omega valve, an essentially isosceles omega, preferably has a blade on its leg, which follows the circumference at the outer radius of the pump chamber and allows the initial entry and passage of the respective blade of the rotor in order to largely evacuate a remaining amount of blood as far as into the omega valve.

The respective omega valve is mounted such that it can rotate or pivot or turn about an eccentric pivot point. With the axial outer edges on both sides, the respective omega valve is placed on the respective axial pump housing closure, for example the housing covers, so that it can be rotated accordingly. For opening, the respective omega valve first moves in the radial direction in such a way that the respective blade of the rotor can pass freely in a synchronized rotation between the rotor and the omega valve, whereby in addition already with the onset of the opening of the sealing valve, the radially sealing contact bends to the housing wall move away with the sealing valve from the pump housing, whereby an active flow around the outer edges of the sealing valve, which is now free on all sides, is ensured, for example above and below as well as laterally of these free spaces to the pump housing. The pump housing is thus widened radially and/or axially, at least in some areas, in the movement area of the at least two sealing valves.

Advantageously, in the area of the respective sealing valve or omega valve, there is a distance radially on the outside and axially between the respective sealing valve or omega valve and the passing blade.

This distance corresponds approximately to or preferably to the free space or the expansion between the respective sealing valve or omega valve and the radial housing wall expanded in the area of the respective sealing valve or omega valve, or the axial housing cover expanded in this area.

With the swirling amount of blood through the free movement on all sides, sufficient restlessness and swirling can be ensured that the formation of thickening blood is not to be expected.

Due to this special design as well as the mounting of the sealing valve, the force vectors occurring in it, pressure and suction, are balanced to zero with themselves, so the pressure and suction forces are largely canceled out during the conveying phase inside and outside of the omega valve. This significantly simplifies the positioning of the omega valve. Furthermore, the energy requirement for holding the omega valve is very low, so that only one guide device for opening and closing, which also determines and secures the position in the open or closed position of the omega valve, is required.

Advantageously, absolute impermeability inside the cardiac pump between the pressure and suction sides is not a requirement. Therefore, side seals are only required on the blades in relevant cases.

Advantageously, a small gap, for example from 0.08 mm to 0.3 mm, is provided between the blades of the rotor and the radial housing wall and the axial housing cover of the pump housing in order to keep blood trauma to minimum. Thus, gentle pumping during rotation but adapted to the rhythm of the human heart is predetermined.

When the respective sealing valve is in a closed state, it rests against the radial housing wall and the axial housing cover as well as the rotor axle tube. However, there can be a small gap at least on the axial housing covers and on the rotor axle tube.

Since the pump housing has electromagnets regularly and/or irregularly distributed at least in the radially outer area over the circumference and/or over the axial extent and/or in the area of the sealing valves, the position and movement of the blades and thus of the rotor can be detected on the one hand, and on the other hand, a simple and contactless drive of the blades and thus of the rotor can also be implemented. Additionally, the position and movement of the sealing valves can also be monitored and controlled.

By having at least one magnet at least at the radially outer end of the blades, the rotational speeds of the rotor and thus the blades and/or the position of the blades in the circumferential direction can be detected. In particular, by means of the magnet(s) on the blade, a drive can be implemented using the electromagnets on the pump housing, which drives the blades and thus the rotor precisely and as required.

By having one, two or more magnets on the at least two sealing valves, they can be controlled in a contactless manner using the electromagnets from outside or inside on the pump housing or from inside using the magnets on the blades. To be able to use electromagnetic fields for the drive unhindered, an appropriate choice, for example, of metallic materials on the one hand or ceramic or fiber-reinforced plastic materials on the other hand is necessary.

Alternatively, the control and operation of the sealing valves can take place mechanically, for example by means of a detent and/or spring force. The respective blade can intervene in a supportive manner. The blade can trigger or assist the opening and/or closing of the sealing valve.

Since the electromagnets can be controlled individually and/or as a group, the control, for example the acceleration, speed, and deceleration, of the sealing valves and/or the blades and thus the rotor can be promoted. Additionally, position monitoring of the sealing valves and/or the blades of the rotor can also be improved. A variable rotating field can be provided by means of the electromagnets.

Since the at least two sealing valves have at least one seal each, the fluid flow is guided in a controlled manner via the inlet openings and outlet openings. These can preferably be present in the area of at least one of the respective radial ends of the sealing valves.

Since the blades protrude radially in the area of the pump housing in the direction of rotation, the respective sealing valves can be moved into a sufficiently or completely open position so that the blades of the rotor can pass without any problems. The control of the respective sealing valves can thus be simplified.

This type of pump is a forced pump, which forcibly sucks in the fluid. To reduce or compensate for more unfavorable pressure conditions, which can also have a negative effect on the periphery, there is an overflow valve as a vacuum-controlled bypass in the respective sealing valve between the pressure or outlet section, i.e., in the direction of rotation in front of the respective sealing valve, and the suction or inlet section, in the direction of rotation behind the respective sealing valve.

By having an overflow valve or vacuum-controlled bypass between the pressure or outlet, i.e., the section that leads the blade in the direction of rotation, and suction or inlet, that is the section that lags the blade in the direction of rotation, alternatively or additionally less favorable pressure conditions can be compensated for, or a targeted overflow effected.

Such a bypass can, however, also be provided on or in the housing or at another point.

Furthermore, alternatively, or additionally, an overflow valve or vacuum-controlled bypass is provided in the blades and/or on the pump housing in the area of the sealing valves from the pressure side to the suction side to compensate for unfavorable pressure conditions or be able to effect a targeted overflow.

The pump according to the invention is a forced pump. With the configuration of such a pump, there is a forced suction, which can lead to an implosion of the ventricles if there is insufficient blood supply in the ventricles. Then a critical state occurs. Advantageously, a vacuum-controlled bypass is provided on or in the pump which, when a predefined negative pressure occurs, prevents a valve, mechanically or electronically controlled, from releasing the bypass between the pressure area and the suction side, and guides blood that has just been pumped back directly to the suction side, thus preventing a further decrease in negative pressure on the suction side. Thus, similarly to the healthy heart, this will cause the known dizziness due to insufficient oxygen-rich blood in the body and especially in the head. However, this will force the body to pause, but would not represent any major threat, until the circulation in the body, after being recognized by the controller, sends an electronic control instruction to the speed of rotation of the pump to normalize the pulse behavior and thus the person's well-being.

More information on this topic may be inferred. When a forced flow pump largely removes the amount of blood to be conveyed from the lower tip of the left ventricle, i.e., the content of 70 cm$^3$ on average corresponding to a healthy heart, there is almost no blood left in this ventricle that can naturally be pumped through myocardial contraction through the aortic valve into the aorta. This means that there is only a residual amount of blood that, above the aortic valve in the very wide aorta, can naturally move very little or not at all, thus leading to congestion. It is known that accumulated or unmoving blood tends to thicken or even clump, which can lead to thrombosis.

In order to prevent this, the known surgical technique of using the known VAD pumps on the lower ventricle will hardly lead to a satisfactory result with regard to the pump presented here. This means that the rotary blade pump according to the invention can, for example, be better placed above the heart muscle such as the aortic valve and at the transition into the aorta. This would restore the natural flow of blood. For example, the atrioventricular valves in the wide aorta would protrude into the inlet tube of the pump and the outlet tube would be encompassed by the other end of the separated aorta above it.

Since the rotary movement or the angular speed of the rotary lobe, that is to say of the rotor and thus of the blades, takes place at different rotational speeds depending on the angular position of the blades, different pressures and flow velocities are achieved. This also means that the rotor can come to a standstill or be stopped for a period of time in order to then accelerate or move again to resume the pumping work.

The rotary movement or the angular speed of the rotary lobe is advantageously reduced when the respective blade is located in the area of the respective sealing valve. Particularly in the area of the sealing valves and when passing the sealing valves, it is advantageous to reduce the rotational speed. It is also advantageous, depending on the inertia and control of the sealing valves, to reduce the rotational speed. It has been shown that with the different rotational speeds and the associated delivery rates, a pulsation of the fluid or blood that is almost comparable to that of the human heart is achieved.

Thus, for example, after a delay in the speed of the blades in the area of and when passing the sealing valves and when the blades or the rotor have accelerated again after having passed the sealing valves, the pumping work is resumed, and a pulse or pulse beat with a heart-like pulse curve is produced.

As an alternative to slowing down, a temporary standstill of the blades in the area of the sealing valves can also be provided.

When the blades are in the area of the sealing valves and pass them, the pumping work is reduced or comes to a standstill. This period of time in which the blades are in the area of the sealing valves or passes them corresponds to about 0.7 to 0.75 times the time for half a revolution, i.e., the path that a blade covers from sealing valve to sealing valve. As is known, the pulsation of the heart takes place at an average of 70 beats per minute, i.e., 0.84 seconds per cardiac work, divided into approx. 0.6 seconds to fill the respective ventricle from the atrium and approx. 0.24 seconds to expel the blood from the respective ventricle into the aorta or pulmonary artery through contraction of the myocardial muscle. In the pump according to the invention, within the said 0.6 seconds, the sealing valve moves approx. 0.1 second to open and remains for approx. 0.4 seconds, then moving to close in another approx. 0.1 seconds by returning to the starting or sealing position. For opening and closing, the sealing valve rotates in the pump housing at an angle of rotation of approx. 110°.

This technical pump can do this work almost equally, in that the pump with the rotor and thus with the two blades overcomes the pump chamber or the pump chamber sections within 0.24 seconds and passes the fluid or blood to the aorta and/or also to the lungs through the known tube prosthesis. Then, the two blades pass the sealing valve or omega valve within 0.6 seconds with the above-described, intrinsically active, pumping interruption that moves the blood on all sides. This also applies to a bilateral heart support measure such as a heart replacement.

In this way, the rotating movement of the blades or the rotor can then start up again and accelerate the pumping work to simulate a pulse that is deceptively similar to the human heartbeat.

The rotary movement of the rotor and/or the position of the sealing valves and/or all other measurement data as the basis for the operation of the pump can be recorded and the operation of the pump can be designed in a controlled manner. For this purpose, the movement, start-up, and acceleration torques that occur are preferably also considered.

The fact that the rotary movement of the rotary lobe and/or the position of the sealing valves is set by means of the drive, preferably by electromagnets, promotes precise interaction between the sealing valves and the blades of the rotor.

By providing an atrioventricular valve in the outlet duct, backflow can be prevented if an unintentionally large amount of blood should back up under the sealing valve when the blades pass through.

Advantageously, early detection of the current pulse of the sinus node and/or the AV node is carried out, this pulse being briefly amplified and sent via a computer interface to the drive unit, for example an electric motor unit or the magnetic control, in order to largely synchronize the artificial heart with the human clock based on the physiological states.

For patients in the northern hemisphere, the cardiac pump preferably does the pumping work with a counter-clockwise rotation, while it works with a clockwise rotation for patients in the southern hemisphere.

The rotary lobe pump can advantageously be used as a cardiac pump to support the human heart or as a bilateral heart substitute.

BRIEF DESCRIPTION OF THE DRAWINGS

Several exemplary embodiments of the invention are shown in the drawings and are described in more detail below, in which.

DETAILED DESCRIPTION OF THE PREFERRED EMBODIMENTS

Figure 1:
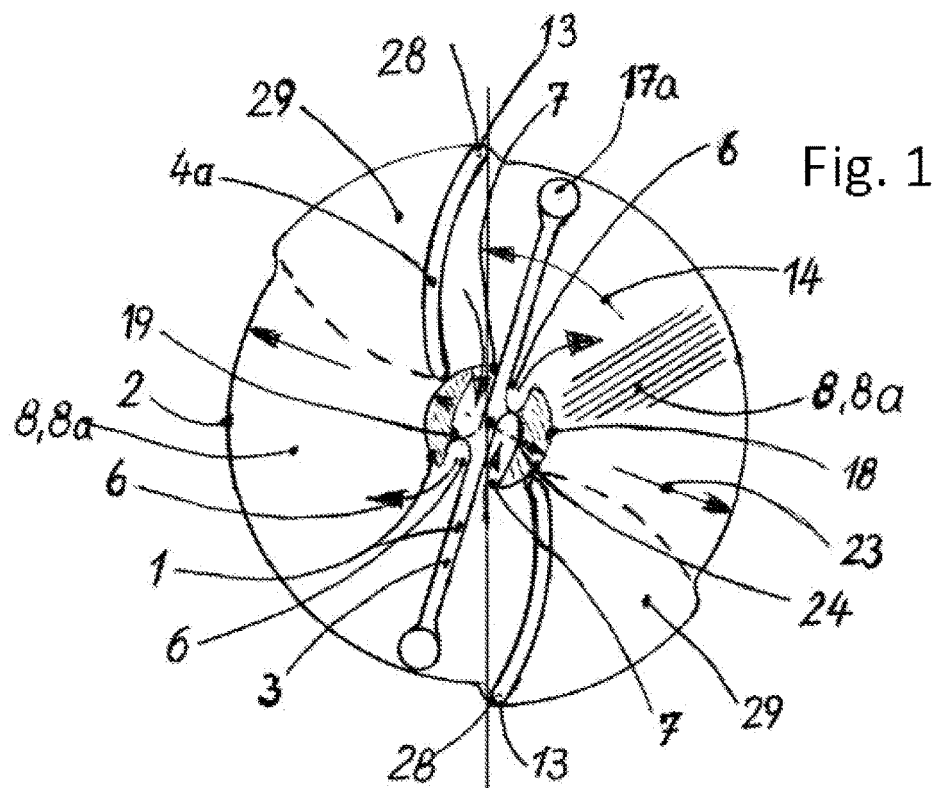
FIG. 1 shows a rotary lobe pump or rotary blade pump as a sectional top view, the blades of the rotor being straight in the radial direction and the sealing valves having an only slightly curved contour, FIGS. 2 to 4 each show a rotary lobe pump or rotary blade pump as a sectional top view in different positions and settings of the rotor and the sealing valves, the blades of the rotor being curved in the radial direction and the sealing valves being curved in a crescent or omega shape.

The basic principle for cardiac support with the rotary lobe pump or rotary blade pump according to the invention is shown, for example, as follows. The fresh blood, for example coming from the lungs, is fed to a central inlet 9, for example in a housing cover 9 at an axial end of the pump housing 2 and an essentially equally large or narrowing inlet duct 11 in a rotor axle tube 18 of a rotating rotor 1 of the rotary lobe pump or rotary blade pump. The blood continues through two inlet openings 6 in the rotor axle tube 18 into the pump chamber 8 or the respective pump chamber sections 8a. As a result of the pumping process, the blood flows from the pump chamber 8 or from the respective pump chamber sections 8a via two outlet openings 7 in the rotor axle tube 18 into the outlet duct 12, which leads to the outlet 10, for example in a further housing cover 10, and out of the pump housing 2 and is fed to the corresponding peripheral blood vessel.

The rotor axle tube 18 of the rotor 1 extends from the inlet 9 at one axial end to an outlet 10 at an opposite end of the rotor axle tube 18. In the rotor axle tube 18, there is a straight or rounded duct separation 19 between inlet 9 and outlet 10 or between inlet duct 11 and outlet duct 12, which runs at an angle to the inlet openings 6 and outlet openings 7 in a flow-promoting manner, thus separating the inlet duct 11 from the outlet duct 12 in the rotor axle tube 18. This fluidically divides the rotor axle tube 18 transversely to the axial extension.

The rotor 1 generates close to 70 pulses per minute, depending on the electronic-electrical control by corresponding revolutions. The blades 3 brush along the housing walls 2 of the pump chamber 8. The housing walls 2 of the pump chamber 8 include the radially outer wall of the pump housing 2 of the pump chamber 8 and the walls of the axial delimitation of the pump chamber 8, for example the inner walls of the housing covers 9, 10 of the pump housing 2. The blades 3 delimit a pressure side 7 from a suction side 6. Since the delivery volume of the pump chamber 8 with the respective pump chamber sections 8a is defined to twice approx. 35 cm$^3$ through the space between the rotor axle tube 18 and the housing walls 2 of the pump chamber 8 and thus, for example, an average of 70 cm$^3$ delivery volume per half revolution, when the rotor 1 or the respective blade 3 rotates in the direction of the respective sealing valve 4a, 4b, pressure 7 occurs in front of the respective blade 3, and suction 6 behind the respective blade 3. The sealing valves 4a, 4b, for example as omega valves 4b, divide the pump chamber 8 into two pump chamber sections 8a and so the conveyed material per pump chamber section 8a is pressed in front of the respective blade 3 through an opening as an outlet opening 7 and into the rotor axle tube 18, and behind the respective blade 3 it is sucked into the respective pump chamber section 8a of the pump chamber 8 through the opening as an inlet opening 6. This results in an average rotational speed of the rotor 1 of 35 rpm for such a solution.

The connection to the vascular system, such as the aorta, is bridged with a vascular prosthesis, as is known per se from the prior art.

The omega valves 4b are advantageously considered as sealing valves 4b, having an extension 36 with an inlet or outlet radius 23 corresponding to the pump chamber outer diameter 23 at least at one radial end of the circular arc sections or the partial cylinder wall, in order to promote the rotary movement of the blade 3 and to still be able to partially convey the respective fluid when retracting.

Furthermore, the pressure conditions in this system are limited, so that the omega valve 4b can be held mechanically or electromagnetically as long as the pump is delivering medium, and thus a pressure force and a suction force act on the respective sealing valve 4a, 4b at the same time. The pressures adequate for the respective vessels and organs come into consideration as the prevailing pressures.

The omega valve 4b can be controlled axially and/or radially. In addition, there is guidance and mounting in or on the axial housing cover 9, 10 of the pump housing 2.

The omega valve 4b can be moved laterally with one of the many mechanical solution options in the housing wall 2 into an expansion 29 or a free space 29 of the pump housing 2 for opening.

Closure can be driven or automatically enforced. For example, this may involve a cam guide mounted in the housing cover 9 and 10 on the rotor axle tube 2, an angle-dependent gear guide or the like, which moves the omega valve 4b depending on the angle of rotation of the rotor 1 and thus the blade 3 to open and close.

The sealing valve 4a, 4b can, depending on the design and if necessary, be locked against the delivery pressure in order to then evade the passage of the blade 3. This can also be done mechanically as well as electromagnetically or similarly controlled.

The sealing valve 4b as an omega valve 4b is shaped or designed in such a way that the pressure forces occurring on it largely cancel each other out or eliminate each other to zero, due to its omega-shaped or circular arc-shaped design with a circular arc of more than 180°.

Since a complete seal between the pressure side 7 and suction side 6 is not necessary inside the cardiac pump, a small gap between the blades 3 of the rotor 1 and the sealing valve 4a, 4b can also be provided against the housing wall 2 of the pump housing 2, which results in less trauma to the blood, which predetermines gently rotary pumping adjusted to human heart.

When the blade 3 passes under or along the open or opening or evaded or evading omega valve 4b, the pump power drops to zero with a fluctuation to be defined over time, with a continued but slowed rotation of the rotor 1 and the blades 3 to achieve strong swirling of the blood. The delivery does not start again until the sealing valves 4a, 4b are closed, for which the respective blade 3 has left the respective range of motion or pivoting range of the respective sealing valves 4a, 4b.

This process of interrupting the delivery takes 0.11 to 0.18 seconds over a range of the angle of rotation of 35° to 50° and a rotational speed of 70 rpm for uniform rotation of a rotor with a blade 3, depending on the design of the individual diameters, namely the pump chamber inner diameter 24 or the rotor axle tube diameter 24 and the pump chamber outer diameter 23, and for example in the case of a blade and a cam design for controlling the omega valve 4b. Pulsation in imitation of the human heart can thus roughly be made possible.

A more precise adjustment of the pumping process to the behavior of the natural heart can be achieved with this pump as follows.

In this relatively slowly rotating system, an electric drive can accelerate or decelerate the rotor 1 in a clocked manner at an average of 70 rpm using one blade 3 or preferably at 35 rpm using two blades 3. Due to the clock frequency and its characteristics, the drive and thus the pump and its pumping work can be individually brought even closer to the human pulse. In the case of one blade 3, the rotational speed is low at approximately 70 rpm for a normal pulse. In the preferred embodiment with two blades 3, the rotational speed is then halved at 35 rpm and can thus be controlled even more precisely, since the double and parallel pumping work within one revolution also generates a pulse rate of 70 and the required pumping volume from two pumping sections of 35 cm$^3$=70 cm$^3$ is reached.

A halved rotation speed of the rotor 1 results from the fact that the rotor 1 has two radially opposite blades 3 and two radially opposed omega valves 4b are also arranged in the pump chamber 8, which are in corresponding movement with mutually canceling pressure ratios. In this variant, the pumping of blood is interrupted over approximately 30 to 50° of a 180° rotation, depending on the selected radii, i.e., the pump chamber outer diameter 23 and the pump chamber inner diameter 24 or rotor axis tube diameter 24. Approx. 28% of the time of a natural pulse beat occurs with acceleration for conveying over approx. 130° to 165° of a 180° rotation in the pump chamber section 8a between the omega valves 4b. In the area of, or under, the respective omega valve 4b, the rotor 1 with its blades 3 slows down considerably at or before passing under it during approx. 72% of the time a natural pulse beat. With the renewed acceleration of the rotor 1 after the respective omega valve 4b over approx. 0.28 times the delivery time or approx. 28% of the amount of time to a pulse beat, a full pump surge is repeatedly initiated and ejected, as this occurs with the natural beat of the heart.

The approx. 72% of the natural pulse beat or heart rhythm is used for collection such as filling the natural ventricle(s) which is specifically accompanied here by the pump by slowing down the passage of the respective blade 3 under the respective omega valve 4b and then the pump withdraws blood from the ventricle on its suction side 6 at the time of the pulse beat. In this way, the pumping work can be synchronized with the rhythm of the natural heart.

The motor power or the motor drive can be ensured with an electric gear motor. A direct electrical drive is better, which can be integrated at the inlet 11 and outlet 12 of the housing covers 9, 10 or directly on the outer circumference of the housing wall 2 of the pump housing 2 to the rotor 1.

On the radial outer edge of the blade 3, magnets 17a can be placed as permanent magnets, which follow a rotating electrical field on the housing cover 9, 10 or on the radially outer wall of the pump housing 2 if electromagnets 16a are installed there and these are controlled accordingly.

The individual flow velocities of the blood in the pump are predetermined in an optimizing manner by the choice of the respective flow cross sections, in particular the inlet opening 6 and the outlet opening 7, in order to additionally ensure sufficient turbulence in the pump through local acceleration.

This pump can also be used as a complete replacement for the human heart. A tandem solution can be implemented for this, which works as a parallel double pump like the single pump described above. One pump takes over the fresh blood from the lungs and the second pump takes over the returning old blood for delivery to the lungs.

An obvious solution to this is one in which a rotor 1 for both conveying directions takes up the fresh blood on one side and directs the blood to the aorta directly in front of the sealing valve 4 through the housing wall 2 or the housing covers 9, 10 to the outside. The old blood is introduced at the opposite end of the tube and then also fed laterally from the pump housing 2 to the lungs or vice versa. The rotor axle tube 18 is closed between the two tube or pump halves by a partition 30. This means that only one motorized solution is required instead of two.

As a specific exemplary embodiment, FIGS. 1 to 4 show a rotary lobe pump or rotary blade pump with a pump housing 2 in a sectional illustration. The pump chamber 8 is essentially cylindrical. A rotary lobe is arranged concentrically as a rotor 1 with two blades 3 lying opposite in the circumferential direction. The rotor 1 with the blades 3 comprises the rotor axle tube 18 or, in other words, the rotor axle tube 18 and the rotor 1 with the blades 3 form a structural unit.

In FIGS. 1 to 4, as described above, the rotor axle tube 18 axially has an inlet duct (not shown) to at least two inlet openings 6 into the pump chamber 8 and an outlet duct (not shown) to at least two outlet openings 7 from the pump chamber 8, each extending separately from the opposite axial ends. One of the inlet openings 6 is arranged in the direction of rotation 14 behind each one of the blades 3 and one of the outlet openings 7 is arranged in the direction of rotation 14 in front of each one in the rotor axle tube 18. Accordingly, in relation to the direction of rotation 14, a pressure side 7 or outlet side 7 is formed in front of the respective blade 3, and, in relation to the direction of rotation 14, a suction side 6 or inlet side 6 is formed behind the respective blade 3.

The sealing valve 4b and the omega valve 4b can be understood as synonymous, so that if the sealing valve 4b is mentioned alone, the omega valve 4b is also included.

The inlet duct (not shown) and the outlet duct (not shown) are separated by means of a duct separation 19 which divides the rotor axle tube 18 into two sections transversely to the axial extension.

Furthermore, two sealing valves 4a, 4b are distributed opposite one another in the circumferential direction. The sealing valves 4a, 4b show the sealing valves 4a, 4b in the radial direction in a contour that is curved or in the shape of a circular arc.

The course of the contour of the sealing valves 4a according to FIG. 1, which is radial to the pump housing 8, is only slightly curved. In particular, the sealing valves 4b shown in FIGS. 2 to 4, as so-called omega valves 4b, have a contour of a circular arc or partial cylinder jacket radially to the pump housing 8, with the circular arc or the partial cylinder jacket formed over 180 degrees and the respective ends of the omega valves 4b having an extension 36 with the inlet or outlet radius 23 corresponding to the pump chamber outer diameter 23 of the housing wall 2 of the pump chamber 8.

In addition, sealing valves 4a, 4b are each designed to be turnable or pivotable or rotatable or displaceable.

According to FIGS. 1 to 4, the sealing valves 4a, 4b are rotatably or pivotably mounted in or on the pump housing 2 via spokes 33 or pins 13 at a pivot point 28 or swivel point 28, the pump housing 2 having at least some free space 29 in some areas radially and axially in the area or range of movement of the two sealing valves 4a, 4b. The radial outer and axial housing wall 2 in the area or movement area of the two sealing valves 4a, 4b thus has an expansion 29 where the respective sealing valves 4a, 4b can at least partially rotate into or rotate through or pivot into, whereby the respective blade 3 can pass along or run along respective sealing valve 4a, 4b or pass the respective sealing valve 4a, 4b at a maximum radial length.

In the specific exemplary embodiment according to FIG. 1, the sealing valves 4a are pivotably mounted on the outer edges 4a in the area of the radially outer housing wall 2 of the pump housing 2 around and via, for example, a continuous pin or two individual pins 13 on the radially outer, pump housing-side end of the sealing valves 4a, so that they can pivot into the free space 29 in the radially outer housing wall 2. The pins 13 are guided or received, for example, in the housing cover 9, 10 which axially delimits the pump housing 2 or the pump chamber 8.

Figure 2:
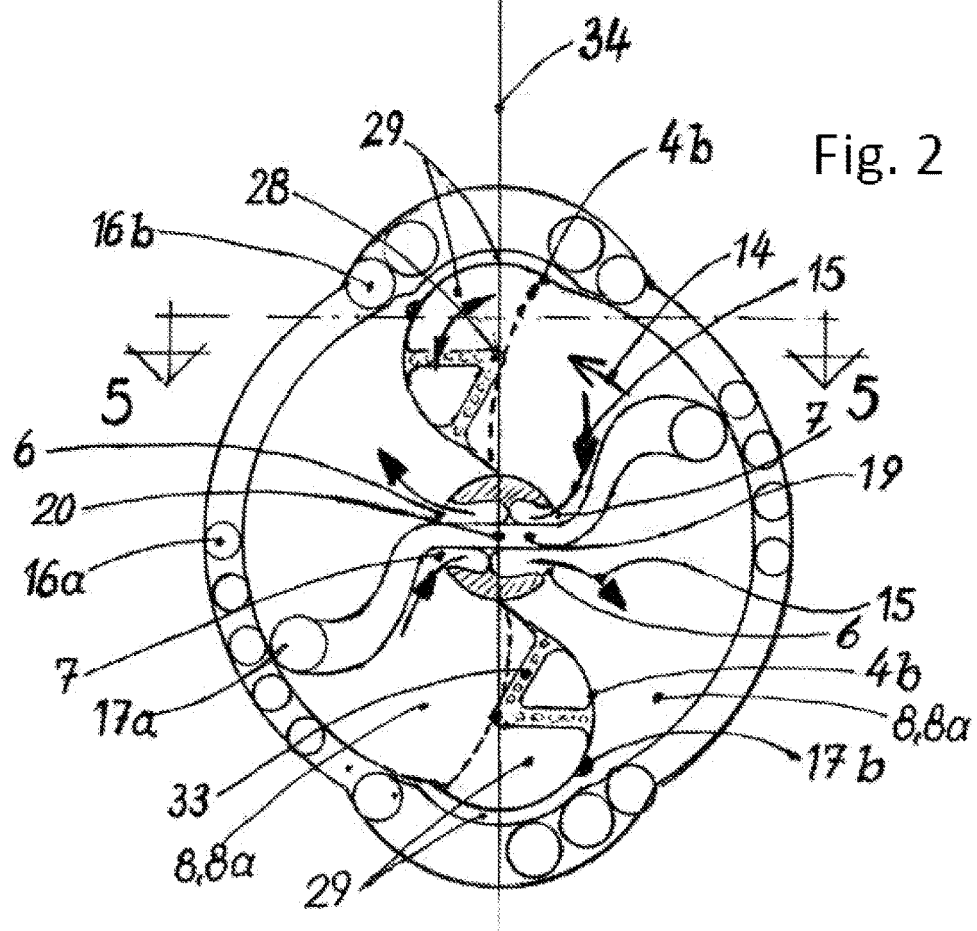
Figure 3:
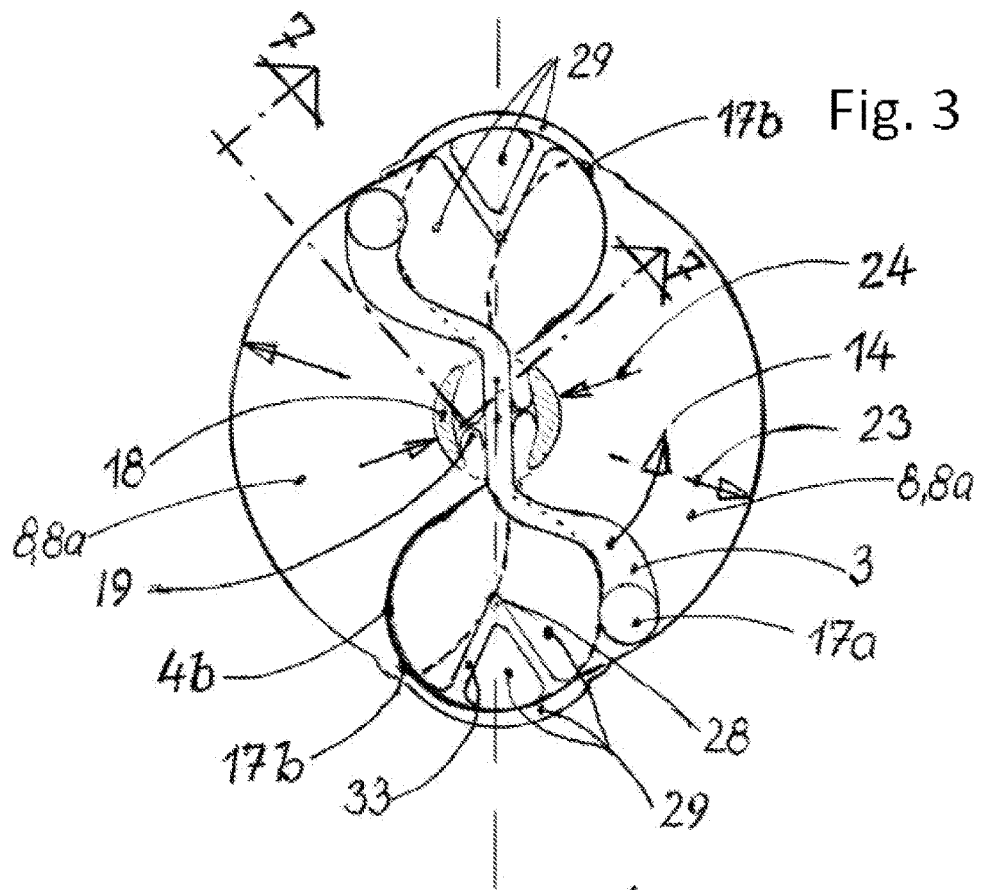
Figure 4:
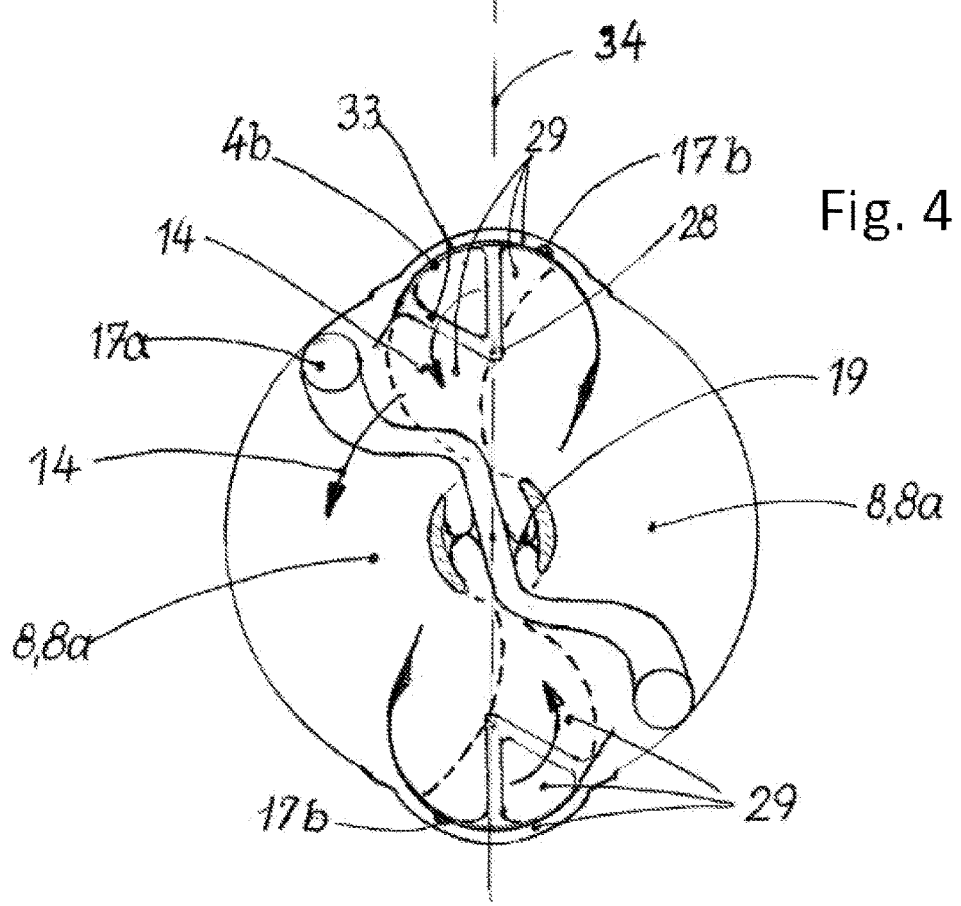

In the embodiment according to FIGS. 2 to 4, the sealing valves 4b are designed as omega valves 4b. The omega valves 4b with a contour of a circular arc or partial cylinder jacket shape are each guided by means of spokes 33 to a pivot point 28 and rotatably mounted at this pivot point 28 via a pin 13 in the housing covers 9, 10 of the pump housing. The circular arc-shaped or partial cylinder jacket-shaped omega valves 4b protrude into a free space 29 or an expansion 29 in the pump housing 2, which is widened for this purpose. In addition to the housing wall 2, the housing covers 9, 10 of the pump housing 2 also have the free space 29 or the expansion 29, in particular in the area of movement of the omega valves 4b and the spokes 33. The respective blade 3 is thus able to brush along or move along the opening omega valve 4b, while the respective omega valve 4b moves or rotates around the end of the respective blade 3 opposite to the direction of movement of the direction of rotation 14 of the blade 3, without causing a collision.

Pump chamber sections 8a are formed by the sealing valves 4a, 4b, with the suction side 6 or inlet side 6 behind the sealing valves 4a, 4b in the direction of rotation 14 and the pressure side 7 or outlet side 7 in front of the sealing valves 4a, 4b.

As described above, the rotational speed of the blades 3 is significantly reduced in the area or movement area of the sealing valves 4a, 4b, which simplifies the synchronization of the respective movements and also prevents collisions.

The free space 29 or the expansion 29 causes the fluid, in particular blood, to swirl when the sealing valves 4a, 4b are opened by the passage of the respective blade 3.

To reinforce this, it is also provided that the pivot point 28 is not arranged centrically but eccentrically in relation to the contour of the circular arc-shaped or partial cylinder jacket-shaped omega valves 4b, the pivot point 28 being selected in such a way that, when the rotary movement or opening movement of the sealing valves 4b or omega valves 4b begins, the latter are released from all the contact points 38 or touch points 38 existing on the circular arc or partial cylinder jacket and thus sealing points 38 to the pump housing 2 and in particular to the housing wall 2, the housing covers 9, 10 and their adjoining regions, and thus the turbulence and circulation set in both at the valve edges and their inner and outer surfaces, in particular caused by the free space 29 or expansion 29 and the free space 37 released between the omega valve 4b and the blade 3.

Figure 7:
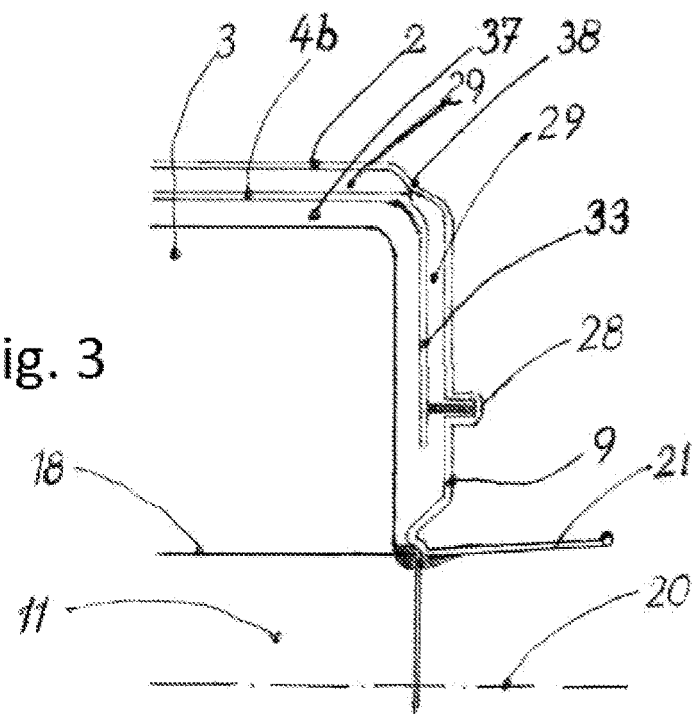
FIG. 7 shows a detailed sectional view of the blade and the sealing valve from FIG. 3

In FIG. 7, a section of a detail from FIG. 3 shows a part of the pump housing 2 with housing wall 2 and a housing cover 9, the sealing valve 4b as an omega valve 4b with spokes 33 which are guided to a pivot point 28, the rotor axle tube 18 with rotor 1 and blade 3 as well as the rotor axle 20 as an axis of symmetry and an inlet tube 21 to the housing cover 9 and rotor axle tube 18 with the inlet duct 11 or inlet 11 to the rotor axle tube 18. In the area of the omega valve 4b and in the area of the spokes 33, there is a free space 29 or an expansion 29 in the pump housing 2. In the corner area or in the transition from the housing wall 2 and to the housing cover 9, when the sealing valve 4b is closed, as an omega valve 4b, a contact point 38 or touch point 38 and thus sealing point 38 between the sealing valve 4b as an omega valve 4b and the pump housing 2, in particular and the respective housing cover 9 is formed.

Furthermore, in the area of the respective sealing valve 4b or omega valve 4b, there is a gap 37 radially on the outside as well as axially between the respective sealing valve 4b or omega valve 4b and the passing blade 3. As shown, the distance 37 corresponds approximately to the free space 29 or expansion 29 between the respective sealing valve 4b or omega valve 4b and the radial housing wall 2 widened in the region of the respective sealing valve 4b or omega valve 4b or the axial housing cover 9 widened in this region.

In order to be able to pass the blade as closely as possible to the contour of the circular arc shaped or partial cylinder jacket shaped omega valves 4b, as shown in FIGS. 2 to 4, the blades 3 have an s-shaped and thus multi-curved course in the radial direction. Advantageously, the curved course of the contour of the blades 3 in the radial direction and the curved course of the contour of the at least two sealing valves 4a, 4b are similar or adapted to each other, so that as much of the fluid as possible, in particular the blood, can still be conveyed before the sealing valve is opened. This equally includes the suction side 6 or inlet side 6 and pressure side 7 or outlet side 7, since the suction 6 and the pressure 7 are effected as long as the sealing valve 4b, as the omega valve 4b, is still closed.

In the specific exemplary embodiment of FIG. 1, the blades 3 are designed to be radially straight, so that they can easily brush or move along the sealing valves 4a, with a large angle of rotation range occurring in this valve solution without conveying, since the sealing valve 4a must already be fully open when the blade 3 starts to enter.

The drive of the blades 3 or the rotor 1 is realized, as shown in FIGS. 1 to 4, by means of magnets 17a on the radial ends of the blades 3 and, as shown in FIG. 2, by means of electromagnets 16a on or in the area of the radial housing wall 2 of the pump housing 2. The electromagnets 16a, 16b can be controlled individually and/or as a group, so that different rotational speeds can be set depending on the angular position of the blades 3, as shown above.

Likewise, magnets 17b are also provided on the sealing valves 4b or omega valves 4b, with which the position of the sealing valves 4b or omega valves 4b can be changed and, if necessary, held, or fixed. Accordingly, electromagnets 16b are provided on the pump housing 2 or on the housing covers 9, 10, which electromagnets can be controlled accordingly, see for example in FIG. 2.

In FIGS. 2 to 4, different operating states or operating positions of the rotary lobe pump or rotary blade pump are shown. While in FIG. 2 the sealing valves 4b are closed and the blades 3 provide both suction 6 and pressure 7 at a high rotational speed, in FIG. 3 the sealing valves 4b are still open after the blades 3 have passed. The speed is still low and can, however, be increased again after the sealing valves 4b are completely closed. In FIG. 4 it is shown that the sealing valves 4b close again and can follow the suction-side contour of the blades 3 in order to close after the blades 3 have rotated slightly further, so that the new pumping process can begin.

Figure 5:
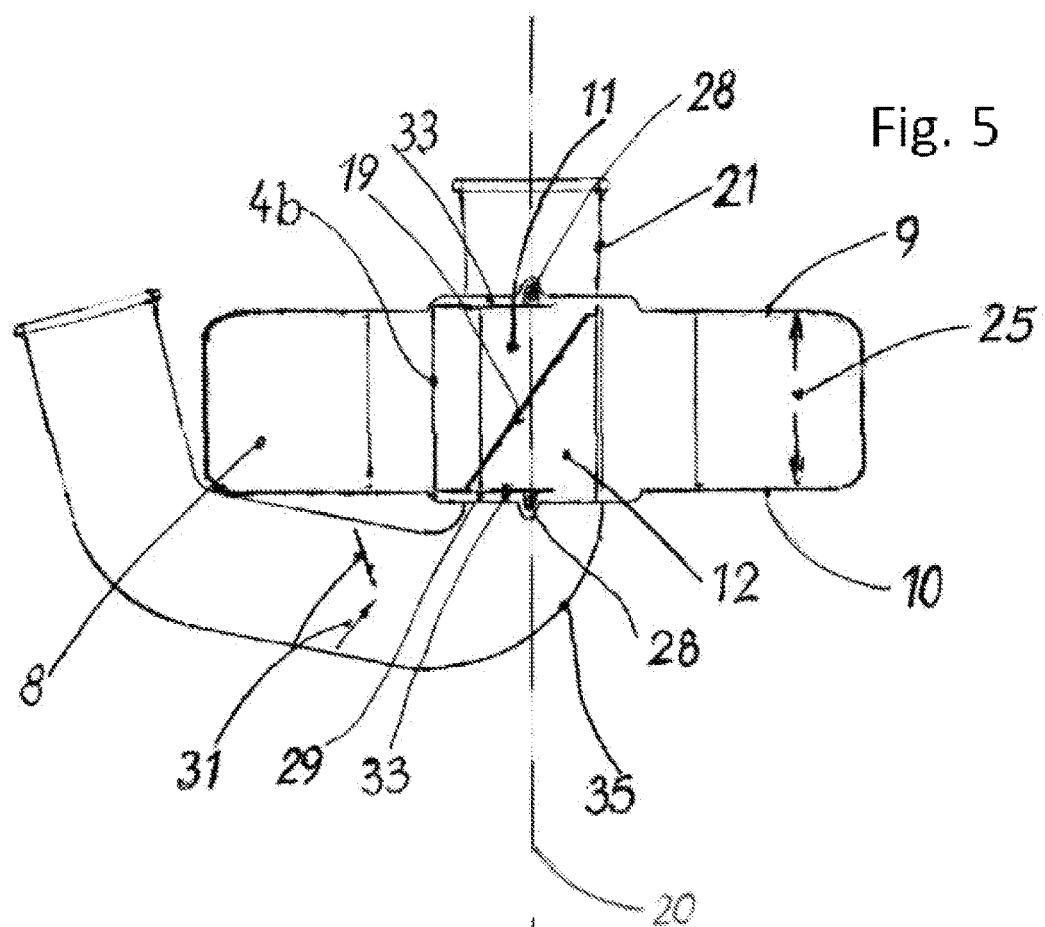
FIG. 5 shows a rotary lobe pump or rotary blade pump as a partial detailed sectional view of FIG. 2 in lateral sectional view.

FIG. 5 shows a sectional view of FIG. 2, where in the area of the omega valve 4b as well as in the area of the spokes 33 in the housing covers 9, 10 of the pump housing 2 there is a free space 29 or expansion 29, where the sealing valve 4b as an omega valve 4b with spokes 33, which are guided to a pivot point 28, is movably arranged. The figure above shows the inlet tube 21 in or on the housing cover 9 as the inlet side, to which the inlet duct 11 in the rotor axle tube 18 connects to the inlet opening (not shown) into the pump chamber 8 with a pump chamber depth 25, which corresponds to the rotor axle tube length. On the outlet side, the outlet opening is not shown in the rotor axle tube 18, to which the outlet duct 12 in the rotor axle tube 18 and the outlet tube 35 shown below in or on the housing cover 10 are connected. In the outlet tube 35, atrioventricular valves 31 are also provided. In the rotor axle tube 18 there is a duct separation 19 which, running at an angle, axially separates the inlet duct 11 from the outlet duct 12.

Figure 6:
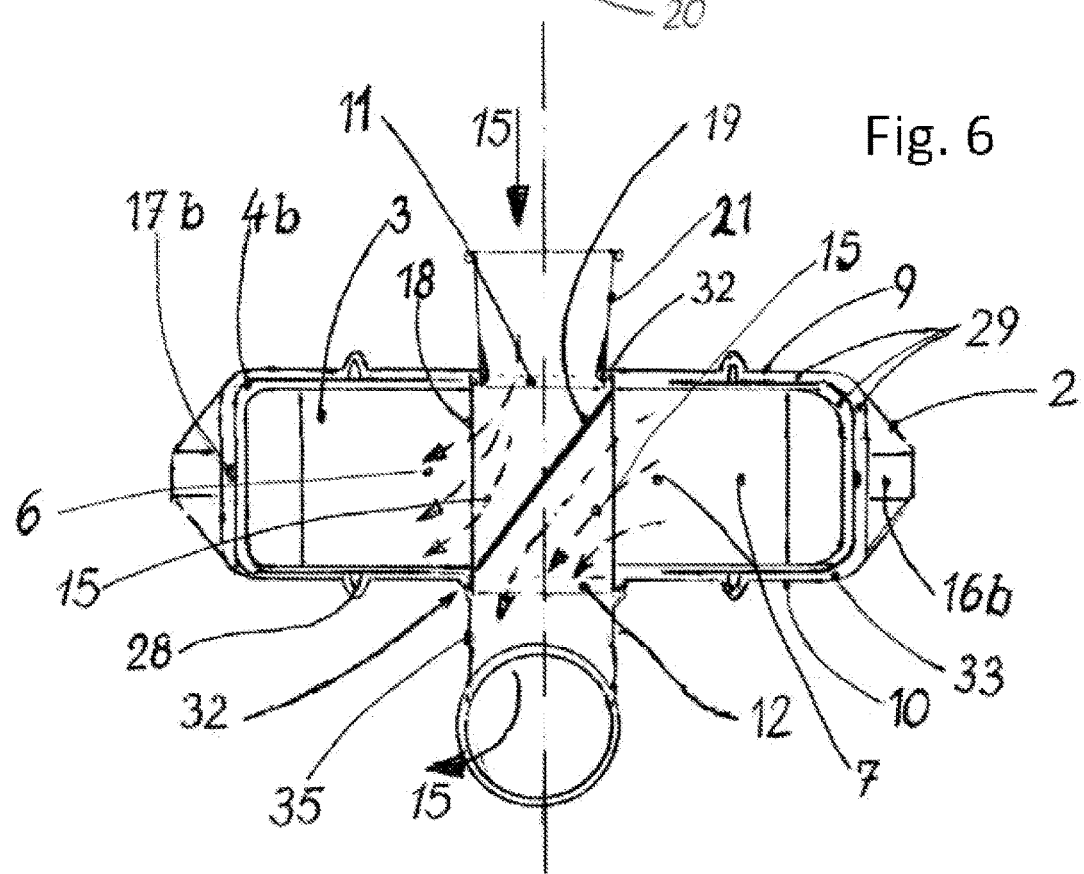
FIG. 6 shows a rotary lobe pump or rotary blade pump in lateral sectional view at the end of conveying, shortly before the sealing valves open.

FIG. 6 shows a rotary lobe pump or rotary blade pump in lateral sectional view at the end of conveying, shortly before the sealing valves 4b open. While the blades 3 still rotate in the direction of the sealing valves 4b, for example as omega valves 4b, which have spokes 33 that are guided to the pivot point 28, fluid or blood still flows in the flow direction 15 into the pump and pump chamber 8 on the suction side 6 of the blades 3 and the sealing valve 4b via the inlet pipe 21, the inlet duct 11 and the inlet opening 6 into the pump chamber 8, while on the pressure side 7 of the blades 3 and the sealing valve 4b, fluid or blood still flows in the flow direction 15 from the pump chamber 8 via the outlet opening 7, the outlet duct 12 and the outlet tube 35. The blades 3 with their magnets (not shown) are controlled accordingly via the electromagnets 16b and initially braked before the sealing valves 4b open. The sealing valves 4b with their magnets 17b are controlled by the electromagnets 16b, so that the sealing valves 4b open in good time and the blades 3 rotate slowly and synchronously with the sealing valves 4b and underneath them. The rotor 1 with the blades 3 has a rotor bearing 32 in the housing covers 9, 10 axially delimiting the pump housing 2 at the transition points between the inlet tube 21 and the rotor axle tube 18 and between the rotor axle tube 18 and the outlet tube 35. The duct separation 19 is also present in the rotor axle tube 18.

Figure 8:
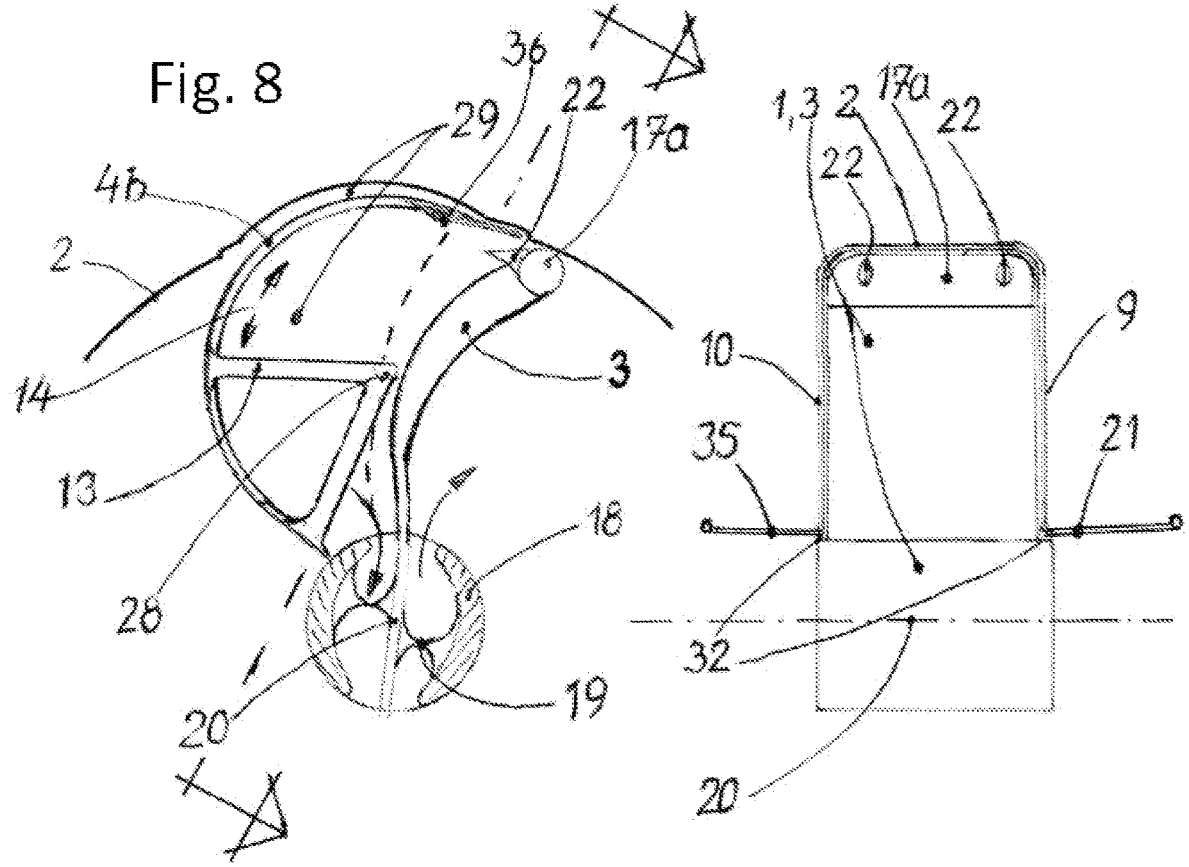
FIG. 8 shows a detailed sectional view of the blade and the sealing valve

In FIG. 8, a further embodiment of a blade 3 is shown, which has a crescent-shaped curved course of the contour opposite to the direction of rotation 14 and protrusions 22 in the form of one or more noses at the radial ends in the direction of rotation, which are capable of pushing an omega valve 4b that may not be in full contact with the radial outer housing wall 2 against the radial outer housing wall 2 to allow free passage of the blade 3.

Furthermore, the approximately tangential extension 36 with the inlet or outlet radius 23 corresponding to the pump chamber outer diameter 23 of the housing wall 2 of the pump chamber 8 or to the pump chamber outer diameter 23 is present on the sealing valve 4b as an omega valve 4b.

The detail also shows a part of the pump housing 2 with the housing wall 2 and the sealing valve 4b as an omega valve 4b with spokes 33 which are guided to a pivot point 28. In the area of the omega valve 4b and in the area of the spokes 33, there is a free space 29 or expansion 29 in the pump housing 2. The duct separation 19 is also present in the rotor axle tube 18. The rotor 1 with the blades 3 has a rotor bearing 32 in the housing covers 9, 10 axially delimiting the pump housing 2 at the transition points between the inlet tube 21 and the rotor axle tube 18 and between the rotor axle tube 18 and the outlet tube 35, as shown in the lateral view in FIG. 8.

Figure 9:
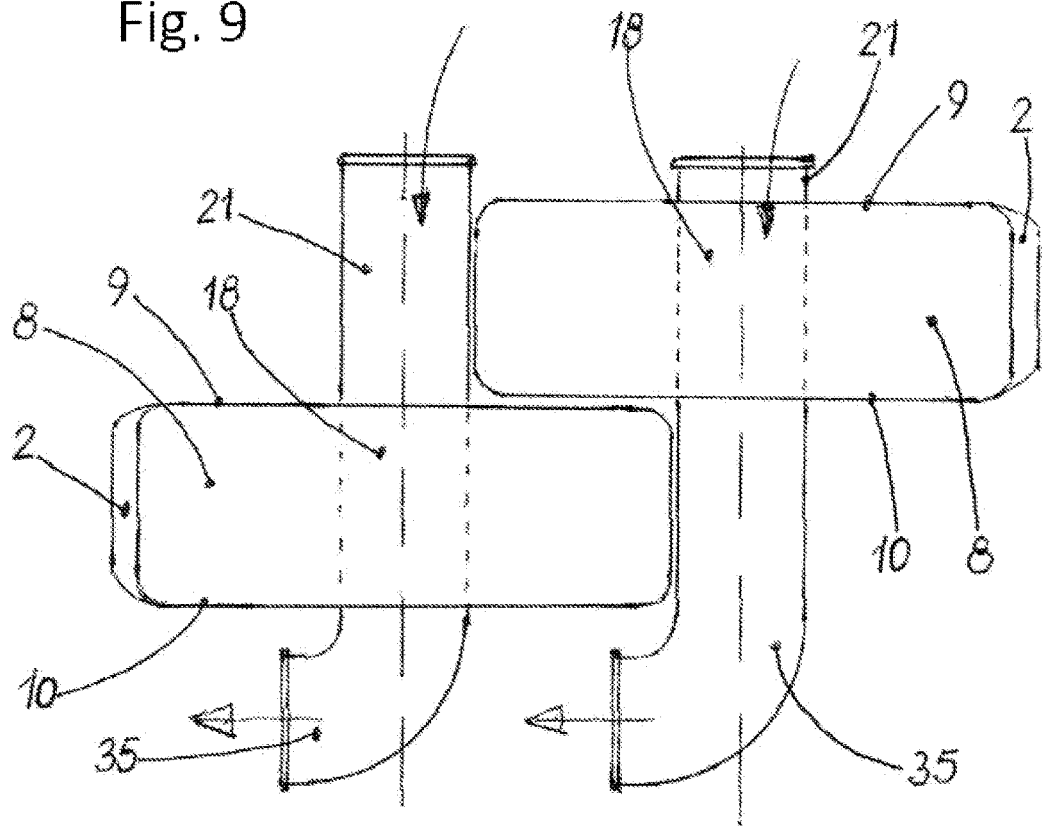
FIGS. 9 and 10, respectively, show a rotary lobe pump or rotary blade pump in lateral sectional view in different positions and settings of the rotor and the sealing valves, wherein the blades of the rotor are curved in radial direction and the sealing valves are curved in sickle or omega shape.
Figure 10:
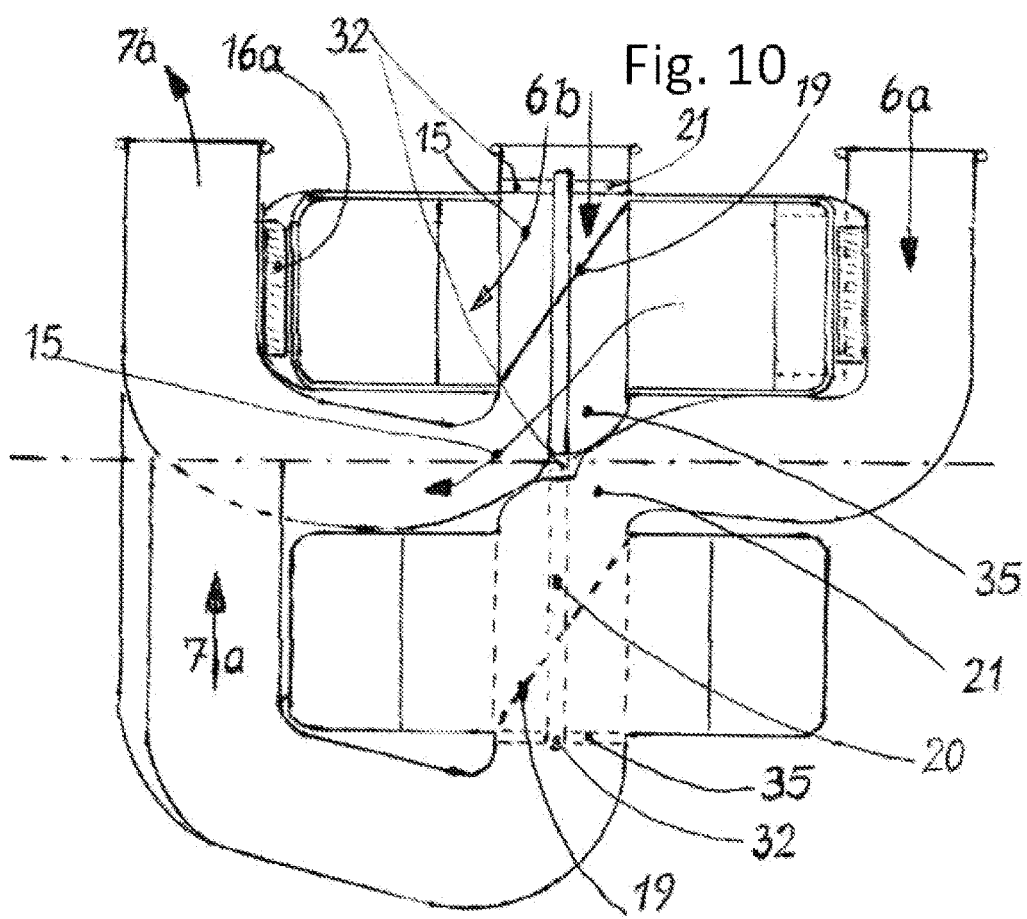

FIGS. 9 and 10 show a combined arrangement of two rotary lobe pumps or rotary blade pumps. In FIG. 9, each of the pumps has its own drive for the rotor 1 or the blades 3. In FIG. 10, there is a common drive for both pumps in the pump shown above, which is constructed as described above, with the drive of the second rotor 1 being effected via the rotor axle 20, which is thus a shaft, and which is at the same time part of the rotor 1. The rotor bearing 32 of the rotor axle 20 is present in the inlet tube 21 of the pump shown above and in the outlet tube 35 of the pump shown below as well as between the pumps in the transition between the outlet tube 35 of the pump shown above and that of the inlet tube 21 of the pump shown below.

For the arrangement, the two rotor axles 20 can be plugged together as shafts. With this arrangement, for example, a full heart replacement can be realized, since both chambers work synchronously, but separately in terms of flow, with blood being conveyed from the mitral valve 6a by the lower pump to the aorta 7a, while blood from the tricuspid valve 6b passes through the upper pump to the pulmonary artery 7b.

Figure 11:
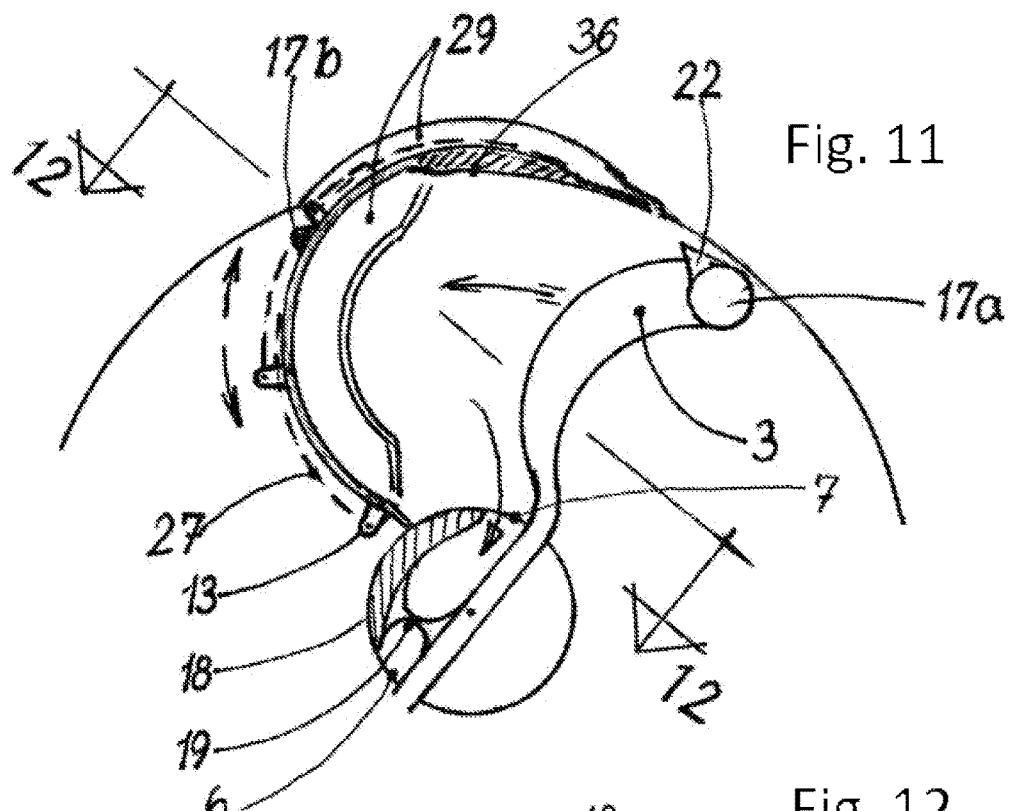
FIG. 11 shows a detailed sectional view of the blade and the sealing valve with an enlarged presentation of the free space at opening of the valve and FIG. 12 shows a lateral sectional view of FIG. 11.
Figure 12:
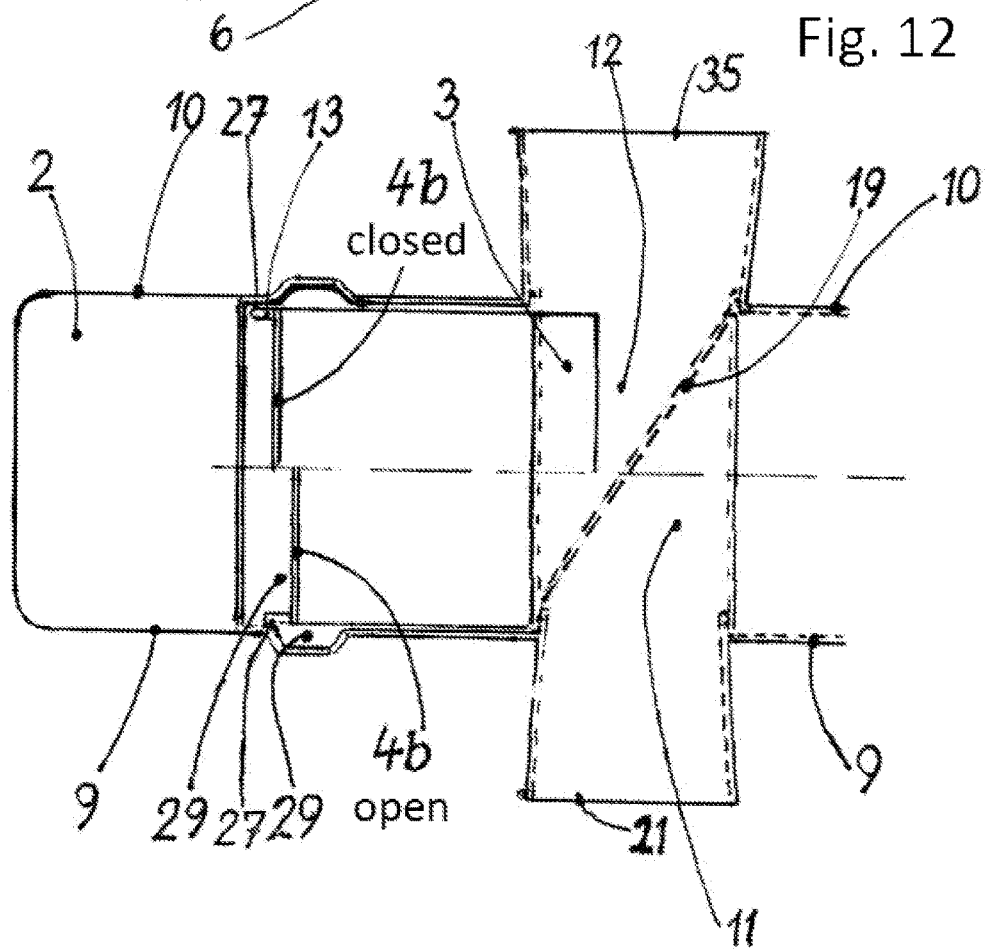

FIGS. 11 and 12 show a further embodiment of the mounting and guidance of the sealing valve 4b or omega valve 4b.

To guide the sealing valve 4b, as shown in FIG. 11, in the housing covers 9, 10 there are guide grooves 27 matching the circular arc shaped or partial cylindrical jacket shaped contour of the sealing valve 4b, the guide grooves 27 being arranged in such a way that there is an eccentric bearing and in the event of a rotary movement the sealing valves 4b move away from at least the radially outer housing wall 2 or the contact arc of the sealing valve 4b with the pump housing 2. For example, there are two or three guide grooves 27 that are not concentric to one another and also each have a narrowing curve.

The sealing valves have webs 13 which include pins 13 or balls 13 which protrude or slide or roll in the guide grooves and thus effect the movement of the sealing valves 4b and their smooth guidance.

As shown in FIG. 12, on the pressure side 7 of the sealing valve 4b in the housing covers 9, 10, along the course of the closed sealing valve 4b, the expansion 29 in the form of a groove in the housing covers 9, 10 is present in the form of an arc only just in front of the sealing contact between the pump housing 2 and the sealing valve 4b. In the closed state, the sealing valve 4b seals on the rotor axle tube 18 and on the housing covers 9, 10 away from the expansion 29 as well as on the radially outer housing wall 2, as shown in the upper half of FIG. 12. When the sealing valve 4b opens, through the non-concentric and also narrowing curve of the guide grooves 27 in the direction of the expansion 29, the sealing valve 4b moves not only away from the rotor axle tube 18, but also in the direction of or over the expansion 29 and also away from the adjacent position on the radially outer housing wall 2, as shown in FIG. 12 in the lower half. This promotes washing around and swirling around the areas of the expansion 29. For the other elements, reference can be made to the preceding explanations.

LIST OF REFERENCE NUMERALS

1—Rotor, rotary blade rotor
2—Pump housing, housing wall
3—Blade
4a—Sealing valve
4b—Sealing valve, omega valve
6—Suction, suction side, inlet, inlet side, inlet opening
6a—from mitral valve
6b—from tricuspid valve
7—Pressure, pressure side, outlet, outlet side, outlet opening
7a—to aorta;
7b—to pulmonary artery
8—Pump chamber
8a—Pump chamber section
9—Housing cover, inlet
10—Housing cover, outlet
11—Inlet duct, rotor axle tube inlet
12—Outlet duct, rotor axle tube outlet
13—Cam, web, valve guide, pin, ball
14—Direction of rotation
15—Direction of flow
16a—Electromagnet, rotor movement
16b—Electromagnet, valve lock
17a—Magnet on the outer edge of blade
17b—Magnet on sealing valve, magnet on omega valve
18—Rotor axle tube
19—Duct separation
20—Rotor axle
21—Inlet tube
22—Protrusion
23—Pump chamber outside diameter, inlet radius, outlet radius
24—Pump chamber inside diameter, rotor axle diameter
25—Pump chamber depth
26—Bypass, valve
27—Guide groove, guides, rail
28—Pivot point, swivel point
29—Free space, expansion
30—Cylinder wall
31—Atrioventricular valve
32—Rotor bearing
33—Spoke
34—Construction axis
35—Outlet tube
36—Extension
37—Distance
38—Contact point, touch point, seal point

The invention claimed is:

1. Rotary lobe pump, comprising a pump housing (2, 9, 10) with an essentially cylindrical pump chamber (8) and a rotary lobe arranged concentrically as a rotor (1) with at least two blades (3) arranged opposite one another or evenly distributed in the circumferential direction and at least two sealing valves (4a, 4b), wherein the blades (3) are point-symmetrical to the axis of rotation of the rotor axle tube (18), characterized in that at least two sealing valves (4a, 4b) arranged opposite one another or evenly distributed in the circumferential direction are provided, the at least two sealing valves (4a, 4b) being rotatable or pivotable and which are curved or sickle-shaped and form the delimitation of the pump chamber and the respective pump chamber section distributed in the circumferential direction, and an inlet duct (11) to at least two inlet openings (6) into the pump chamber (8) and an outlet duct (12) from at least two outlet openings (7) out of the pump chamber (8) being provided axially in a rotor axle tube (18), extending from the opposite axial ends and separated from one another, one of the inlet openings (6) being arranged behind each one of the blades (3) in the rotor axle tube (18) in the direction of rotation (14) and one of the outlet openings (7) being arranged in front of each blade in the direction of rotation (14).

2. Method for operating a rotary lobe pump according to claim 1, in particular as a cardiac pump to support the human heart or as a heart substitute, wherein in a substantially cylindrical pump chamber (8) of a pump housing (2) by the rotary movement of a rotary lobe arranged concentrically as a rotor (1) with a rotor axle tube (18) and with at least two blades (3) arranged opposite one another or evenly distributed in the circumferential direction, wherein the blades (3) are point-symmetrical to the axis of rotation of the rotor axle tube (18), a fluid is pressed into an outlet opening (7) in the rotor axle tube (18) in the direction of rotation (14) in front of the respective blade (3) and at the same time the fluid is sucked in through an inlet opening (6) in the rotor axle tube (18) in the direction of rotation (14) behind the respective blade (3), with a separation of the areas of pressure (7) or outlet (7) and suction (6) or inlet (6) respectively taking place by means of a sealing valve (4a, 4b) and the respective sealing valve (4a, 4b) being in a closed position for pressure (7) or outlet (7) and suction (6) or inlet (6), and after the pressure (7) or outlet (7) as well as after the suction (6) or inlet (6) the respective sealing valve (4a, 4b) is pivoted to the radially outer area of the pump chamber (8) or rotated around the radially outer end of the respective blade (3) to allow passage of the respective blade (3), and when the blade has passed, the respective sealing valve (4a, 4b) is moved back into a closed position and then the pressure (7) or outlet (7) and suction (6) or inlet (6) take place again, wherein the rotary motion of the rotary lobe as rotor (1) is reduced when the respective blade (3) is located in the region of the respective sealing valve (4a, 4b).

3. Method according to claim 2, characterized in that
the rotary movement of the rotary lobe as a rotor (1) takes place at a different rotational speed depending on the angular position of the blades (3).

4. Method according to claim 2, characterized in that
the setting of the rotary movement of the rotary lobe as rotor (1) and/or position of the sealing valves (4a, 4b) is carried out by means of the actuation of electromagnets (16a, 16b) and/or in that the rotary movement of the rotor (1), the position of the sealing valves (4a, 4b) and/or further data are detected as a basis for the operation of the pump and the operation of the pump is controlled.

5. Rotary lobe pump according to claim 1, characterized in that
the contour of the blades (3) has a single or multiple curvature in the radial direction.

6. Rotary lobe pump according to claim 1, characterized in that
the contour of the at least two sealing valves (4a, 4b) has a curved or arcuate shape in the radial direction.

7. Rotary lobe pump according to claim 1, characterized in that
the radially curved course of the contour of the blades (3) and the curved course of the contour of the at least two sealing valves (4a, 4b) are similar or adapted or congruent to each other.

8. Rotary lobe pump according to claim 1, characterized in that
the at least two sealing valves (4a, 4b) have, at least at the end facing the radially outer housing wall (2) of the pump chamber (8), an approximately tangentially rectilinear extension (36) or an extension (36) with an inlet or outlet radius (23) corresponding to the pump chamber outer diameter (23) of the housing wall (2) of the pump chamber (8) or a pump chamber outer diameter (24).

9. Rotary lobe pump according to claim 1, characterized in that
the at least two sealing valves (4a, 4b) in or on the pump housing (2) are mounted or arranged such that they can slide or rotate or pivot on a pivot point (28) or swivel point or in rails (27) or in or on guides (27) via spokes (33) or webs (35) or cams (13) or pins or balls, the pump housing (2) having at least some free space (29) radially and/or axially in some places at least in the area or movement region of the at least two sealing valves (4a, 4b).

10. Rotary lobe pump according to claim 1, characterized in that
the at least two sealing valves (4a, 4b) are concentrically or eccentrically rotatable or pivotable or rotatable.

11. Rotary lobe pump according to claim 1, characterized in that
the pump housing (2) has electromagnets (16a, 16b) distributed evenly and/or irregularly at least in the radially outer region over the circumference and/or over the axial extension and/or in the region of the sealing valves (4).

12. Rotary lobe pump according to claim 1, characterized in that
at least one magnet (17b) is present on the at least two sealing valves (4a, 4b) and/or in that at least one magnet (17a) is present at least at the radially outer end of the blades.

13. Rotary lobe pump according to claim 1, characterized in that
electromagnets (16a, 16b) can be controlled individually and/or as a group.

14. Rotary lobe pump according to claim 1, characterized in that
the at least two sealing valves (4a, 4b) each have at least one seal and/or one overflow valve (26) or vacuum-controlled bypass (26) in the respective sealing valve (4a, 4b) or on or in the housing (2) or rotor (1) between pressure (7) or outlet (7) and suction (6) or inlet (6).

15. Rotary lobe pump according to claim 1, characterized in that
the blades have a protrusion (22) radially in the region of the pump housing in the direction of rotation (14) and/or in that the blades (3) and/or the pump housing (2) have an overflow valve (26) or vacuum-controlled bypass (26) between pressure (7) or outlet (7) and suction (6) or inlet (6) in the region of the sealing valves (4a, 4b).

16. Rotary lobe pump according to claim 1, characterized in that
that the outlet duct (12) or the rotor axle tube (12) for the outlet or the outlet tube (35) has a winding or helical course or inner cross-section.

17. Use of the rotary lobe pump according to claim 1 as a cardiac pump for supporting the human heart or as a heart substitute.

\* \* \* \* \*